United States Patent
Cohen et al.

(10) Patent No.: US 11,058,496 B2
(45) Date of Patent: Jul. 13, 2021

(54) REGISTERING PROBE AND SHEATH IMAGES ON A DISPLAY

(71) Applicant: BIOSENSE WEBSTER (ISRAEL) LTD., Yokneam (IL)

(72) Inventors: Shmuel Cohen, Yokneam Illit (IL); Lior Zar, Poria Illit (IL); Assaf Pressman, Pardes Hanna-Karkur (IL); Konstantin Feldman, Haifa (IL); Daniel Osadchy, Haifa (IL); Oshrat Ben Zaken, Shimshit (IL); Shiran Eliyahu, Yokneam Illit (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 384 days.

(21) Appl. No.: 15/650,053

(22) Filed: Jul. 14, 2017

(65) Prior Publication Data
US 2018/0042683 A1 Feb. 15, 2018

Related U.S. Application Data (60) Provisional application No. 62/375,234, filed on Aug. 15, 2016.

(51) Int. Cl.
*A61B 34/20* (2016.01)
*A61B 5/06* (2006.01)
*G01S 5/16* (2006.01)

(52) U.S. Cl.
CPC .............. *A61B 34/20* (2016.02); *A61B 5/062* (2013.01); *A61B 5/068* (2013.01); *G01S 5/16* (2013.01);
(Continued)

(58) Field of Classification Search
None
See application file for complete search history.

(56) References Cited

U.S. PATENT DOCUMENTS 6,263,230 B1 * 7/2001 Haynor .................. A61B 5/062
128/899
8,478,379 B2 7/2013 Osadchy et al.
(Continued)

FOREIGN PATENT DOCUMENTS

EP 2 376 935 B1 11/2013
EP 2376935 B1 * 11/2013

OTHER PUBLICATIONS

European Search Report dated Jan. 17, 2018 from corresponding European Patent Application No. 17186174.3.

*Primary Examiner* — Lina M Cordero
*Assistant Examiner* — Brandon J Becker
(74) *Attorney, Agent, or Firm* — Dergosit & Noah LLP; Todd A. Noah (57) ABSTRACT

A method, including calculating locations of first sensors attached to a probe that has been inserted into a human patient, and calculating positions of second sensors attached to a sheath via which the probe is inserted. The method also includes calculating respective shapes of the probe and the sheath, to achieve a best fit to the calculated probe sensor locations and sheath sensor positions, while restricting the probe to pass through the sheath. The calculated respective shapes of the probe and the sheath are used to present an image of the sheath aligned with the probe.

16 Claims, 9 Drawing Sheets

(52) U.S. Cl.
CPC ........ *A61B 2034/2051* (2016.02); *A61B 2034/2065* (2016.02)

(56) References Cited

U.S. PATENT DOCUMENTS

| | | | | |
|---|---|---|---|---|
| 8,818,486 B2* | 8/2014 | Montag | ............... | A61B 5/062 |
| | | | | 600/409 |
| 2003/0152256 A1* | 8/2003 | Kira | ............... | B82Y 30/00 |
| | | | | 382/129 |
| 2005/0228404 A1* | 10/2005 | Vandevelde | ............... | A61B 34/20 |
| | | | | 606/130 |
| 2010/0204569 A1* | 8/2010 | Burnside | ............... | A61B 8/0841 |
| | | | | 600/424 |
| 2013/0345718 A1* | 12/2013 | Crawford | ............... | A61B 17/025 |
| | | | | 606/130 |
| 2014/0213906 A1* | 7/2014 | Li | ............... | A61B 8/4218 |
| | | | | 600/459 |
| 2014/0350401 A1* | 11/2014 | Sinelnikov | ............... | A61B 17/2202 |
| | | | | 600/439 |
| 2016/0066770 A1* | 3/2016 | Barbato | ............... | A61B 1/00167 |
| | | | | 600/138 |
| 2017/0181706 A1* | 6/2017 | Montag | ............... | A61B 5/6852 |

* cited by examiner

REGISTERING PROBE AND SHEATH IMAGES ON A DISPLAY

CROSS-REFERENCE TO RELATED APPLICATION

This application claims the benefit of U.S. Provisional Patent Application 62/375,234, filed 15 Aug. 2016, which is incorporated herein by reference.

FIELD OF THE INVENTION

The present invention relates generally to presentation of images on a display, and specifically to correction of misaligned images, and presentation of the corrected images on the display.

BACKGROUND OF THE INVENTION

During an invasive medical procedure, it is important to track items, such as catheters or probes that have been inserted into a patient undergoing the procedure. The catheters or probes may be inserted via a sheath which has been pre-positioned in the patient, and it is also important to track the sheath.

While the tracking of the items is typically performed automatically by equipment specifically designed for this purpose, it is essential that a professional performing the procedure is aware of the locations of the tracked items. This is typically implemented by displaying images of the tracked items in registration with each other, and in registration with an image of the region where the items are situated.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

calculating locations of first sensors attached to a probe that has been inserted into a human patient;

calculating positions of second sensors attached to a sheath via which the probe is inserted;

calculating respective shapes of the probe and the sheath, to achieve a best fit to the calculated probe sensor locations and sheath sensor positions, while restricting the probe to pass through the sheath; and using the calculated respective shapes of the probe and the sheath to present an image of the sheath aligned with the probe.

Typically, calculating the locations of the first sensors attached to the probe includes positioning at least one magnetic sensor on the probe, and calculating the locations using a magnetic tracking system.

Typically, calculating the positions of the second sensors includes positioning at least one electrode on the sheath, generating a plurality of currents from the at least one electrode, and calculating the positions in response to the plurality of currents in a current tracking system.

In a disclosed embodiment calculating the respective shapes of the probe and the sheath includes modeling the probe and the sheath as a single shaft. The first sensors may be fixed on the shaft. The second sensors may be free to slide on the shaft.

In a further disclosed embodiment calculating the respective shapes of the probe and the sheath includes using a cost function to calculate the respective shapes.

A slide variable having a value related to a distance between distal ends of the probe and the sheath may be incorporated into the cost function. A minimum value of the slide variable may correspond to a distal tip of the probe being inside the sheath. A maximum value of the slide variable may correspond to the first sensors and the second sensors being separated by no more than a preset distance.

There is further provided, according to an embodiment of the present invention, apparatus, including:

a probe configured to be inserted into a human patient;

first sensors attached to the probe;

a sheath via which the probe is inserted;

second sensors attached to the sheath; and a processor, configured to:

calculate locations of the first sensors attached to the probe, calculate positions of the second sensors attached to the sheath, calculate respective shapes of the probe and the sheath, to achieve a best fit to the calculated probe sensor locations and sheath sensor positions, while restricting the probe to pass through the sheath, and use the calculated respective shapes of the probe and the sheath to present an image of the sheath aligned with the probe.

The present disclosure will be more fully understood from the following detailed description of the embodiments thereof, taken together with the drawings, in which:

DETAILED DESCRIPTION OF EMBODIMENTS

Overview

As explained above, during an invasive medical procedure, it is important to track items, such as catheters or probes that have been inserted into a patient undergoing the procedure. Any misalignment of the images of the items is at least inconvenient to the professional performing the procedure, and may even lead to errors in placement of the tracked items.

In the case of a probe that is inserted via a sheath, the probe and sheath are inherently in registration. Embodiments of the present invention use this inherent registration to correct any misalignment of the images of the probe and the sheath.

Thus, an embodiment of the present invention provides a method that calculates locations of first sensors, typically magnetic sensors and/or electrodes, attached to a probe that has been inserted into a human patient. Positions of second sensors, typically electrodes, attached to a sheath via which the probe is inserted are also calculated.

Respective shapes of the probe and the sheath, to achieve a best fit to the calculated probe sensor locations and sheath sensor positions, while restricting the probe to pass through the sheath, are then calculated. The calculated shapes of the probe and of the sheath are then used to present an image of the sheath aligned with the probe.

DESCRIPTION OF EMBODIMENTS

In the following description, like elements in the drawings are identified by like numerals, and the like elements are differentiated as necessary by appending a letter to the identifying numeral.

Figure 1A:
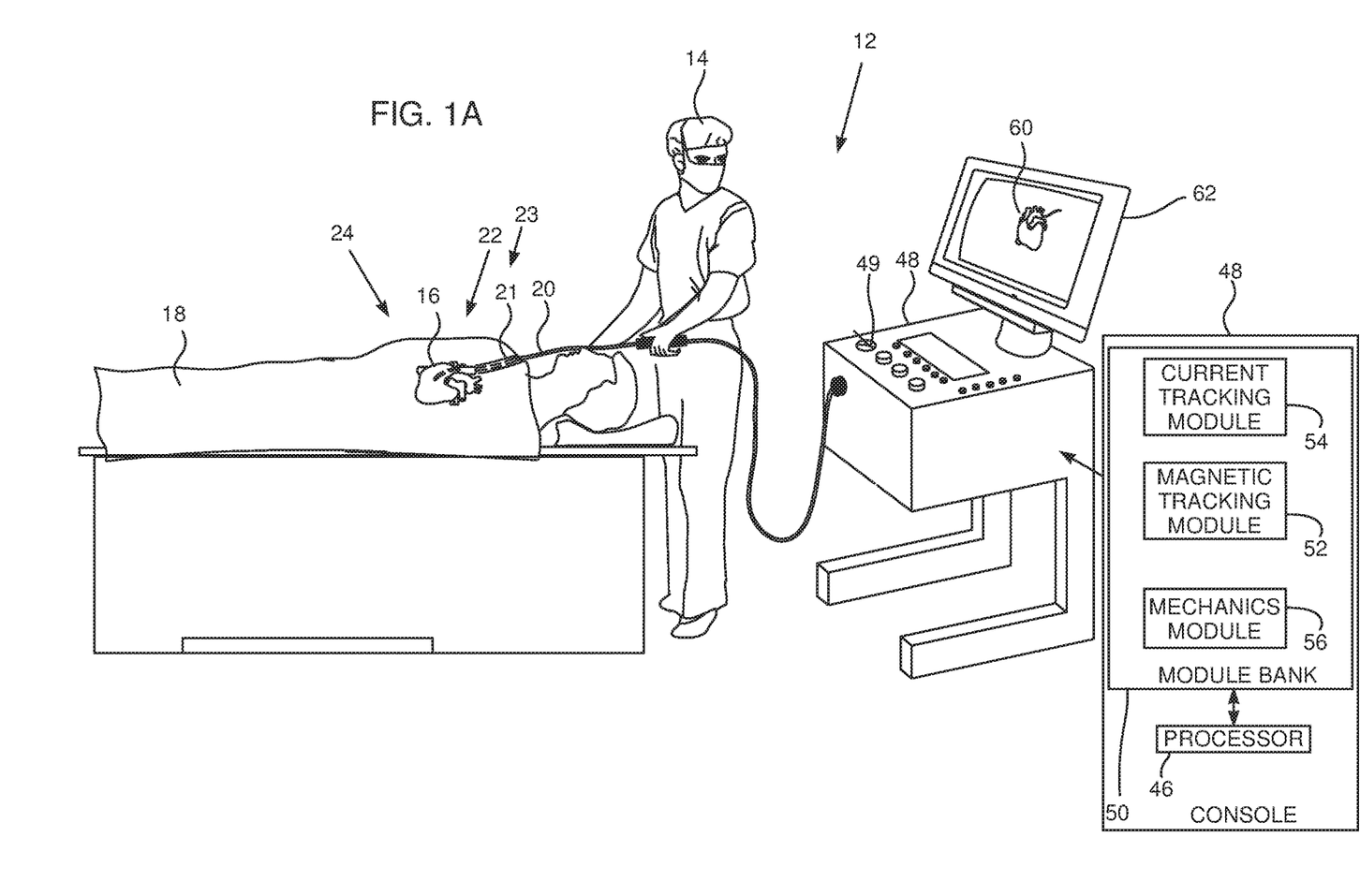
FIGS. 1A, 1B, and 1C are schematic illustrations of an invasive medical procedure, according to an embodiment of the present invention.
Figure 1B:
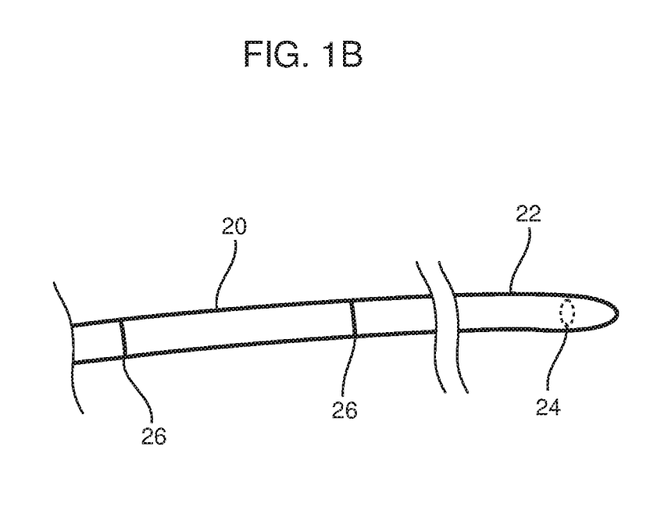
Figure 1C:
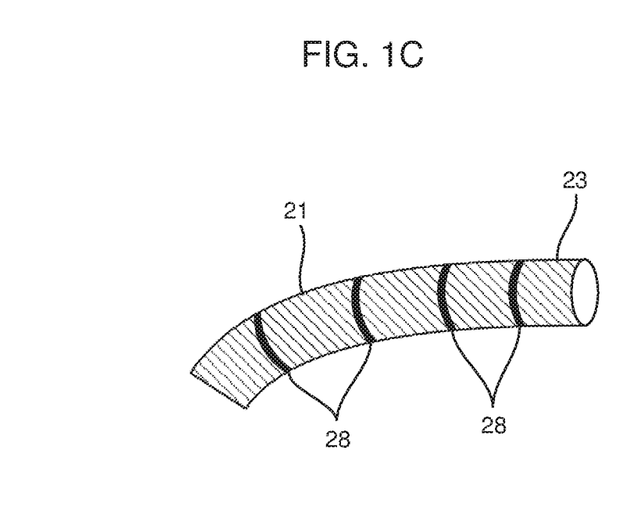

FIGS. 1A, 1B and 1C are schematic illustrations of an invasive medical procedure using apparatus 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a probe 20 into a sheath 21 that has been pre-positioned in a lumen of the patient. Sheath 21 is positioned so that a distal end 22 of the probe may enter the heart of the patient, after exiting a distal end 23 of the sheath. FIG. 1B and FIG. 1C respectively show details of probe 20 and sheath 21.

Probe 20 may comprise any type of catheter that can be inserted into the heart of the patient, and that can be tracked using a magnetic tracking system and/or an impedance measuring system, both of which systems are described further below. For example, probe 20 may comprise a shaft-like catheter, a lasso catheter, or a pentaray catheter, produced by Biosense Webster of Diamond Bar, Calif., or catheters generally similar to these catheters. In order to be tracked by the magnetic tracking system the probe has at least one magnetic sensor, and in order to be tracked by the impedance measuring system the probe has at least one electrode.

For clarity and simplicity, in the following description probe 20 is assumed to have a generally cylindrical structure, with a magnetic sensor 24 at its distal tip 22, and multiple electrodes 26 on elements of the probe proximal from the distal tip, as is illustrated in FIG. 1B. Those having ordinary skill in the art will be able to adapt the description, mutatis mutandis, for probes having only magnetic sensors, probes having only electrodes, and probes having combinations of magnetic sensors and electrodes other than that exemplified here, and all such probes are assumed to be comprised within the scope of the present invention.

Apparatus 12 is controlled by a system processor 46, which is located in an operating console 48 of the apparatus. Console 48 comprises controls 49 which are used by professional 14 to communicate with the processor. During the procedure, processor 46 communicates with a magnetic tracking module 52 and a current tracking module 54 in a module bank 50, in order to track locations and orientations of elements of the probe.

Module 52 enables the processor to use a magnetic tracking method, wherein magnetic transmitters external to patient 18 generate signals in sensor 24. Sensor 24 is typically a single axis sensor (SAS) or a triple axis sensor (TAS), both of which are well known in the art. The signals generated by the sensor, in response to magnetic fields traversing the sensor, allow the sensor to act as a location and orientation transducer for the element of the probe, in this case the distal tip, where the sensor is situated. The Carto® system produced by Biosense Webster, of Diamond Bar, Calif., uses such a tracking method.

Module 54 enables the processor to use a current tracking method, which measures currents between electrodes 26 of the probe and electrodes on the skin of patient 18. The processor and module 54 use the measured currents, or corresponding impedances, to generate coordinates of locations of elements of the probe where the electrodes are situated. The Carto® system also uses such a current tracking method.

The processor may then apply the tracked positions (locations and orientations) of all the probe elements, together with mechanical properties of the probe, to compute corrected coordinates for the elements using a mechanics module 56. The module also generates data for a graphical representation of the probe using the corrected coordinates. The graphical representation follows a three-dimensional (3D) line that joins the corrected coordinates.

Module 56 uses a method for computing a graphical representation that is described in U.S. Pat. No. 8,478,379 to Osadchy et al., and which is incorporated herein by reference. The method uses mechanical properties of the probe, as well as known locations and orientations of position transducers within the probe, to compute a cost function giving a corrected shape for the probe, and a description of such a method is provided in Appendix A. The Carto® system also uses such a graphical representation method.

Sheath 21 (FIG. 1C) may be any type of tubular structure that can be inserted into a lumen of a patient, and which is able to allow passage of probe 20 within a tube formed by the sheath. As for probe 20, one or more magnetic sensors and/or one or more electrodes may be incorporated into the sheath, and may respectively be tracked by the magnetic tracking system and impedance measuring system described above.

For clarity and simplicity, in the following description sheath 21 is assumed to have multiple electrodes 28 on distal end 23 of the sheath, and no magnetic sensors. In one embodiment there are four electrodes 28. Those having ordinary skill in the art will be able to adapt the description, mutatis mutandis, for sheaths having only magnetic sensors, and for sheaths having multiple magnetic sensors and multiple electrodes, and all such sheaths are assumed to be comprised within the scope of the present invention.

The processor and module 54 use the measured currents from electrodes 28, or corresponding impedances for the electrodes, to generate coordinates of a location and an orientation of the distal end of sheath 21.

As for the coordinates of the probe, the processor may then correct the coordinates of the sheath distal end, using mechanics module 56 and mechanical properties of the sheath, to generate corrected coordinates of the sheath. The corrected coordinates may also be used to generate data for a graphical representation of the sheath.

The software for processor 46 and bank 50 may be downloaded to the processor in electronic form, over a network, for example. Alternatively or additionally, the software may be provided on non-transitory tangible media, such as optical, magnetic, or electronic storage media.

In order to operate apparatus 12, bank 50 typically comprises modules other than those described above, such as a force module for measuring the force on distal end 22, and an irrigation module allowing the processor to control irrigation provided for the distal end. For simplicity, such other modules are not illustrated in FIG. 1A. All modules may comprise hardware as well as software elements.

The two tracking methods, i.e., the magnetic tracking method using module 52 and the current tracking method using module 54, are typically registered together, so that locations and orientations generated by one system correspond with locations and orientations generated by the other system. Appendix B describes how a probe such as probe 20 registers the two tracking methods to produce a calibration map.

Processor 46 uses the coordinates of locations and orientations calculated by the modules to display images of probe 20 and sheath 21 on a three-dimensional map 60 of the heart of the patient, which is presented on a screen 62. However, notwithstanding applying the registration method described above, or another registration method known in the art, there are typically discrepancies between the calculated location and/or orientation coordinates of the probe and of the sheath. The discrepancies typically lead to misalignment of the images of the probe and sheath. Embodiments of the present invention overcome such misaligned images, by constructing and using a theoretical hybrid probe/sheath model, and using the model to calculate probe and sheath curves, as is described below.

Figure 2:
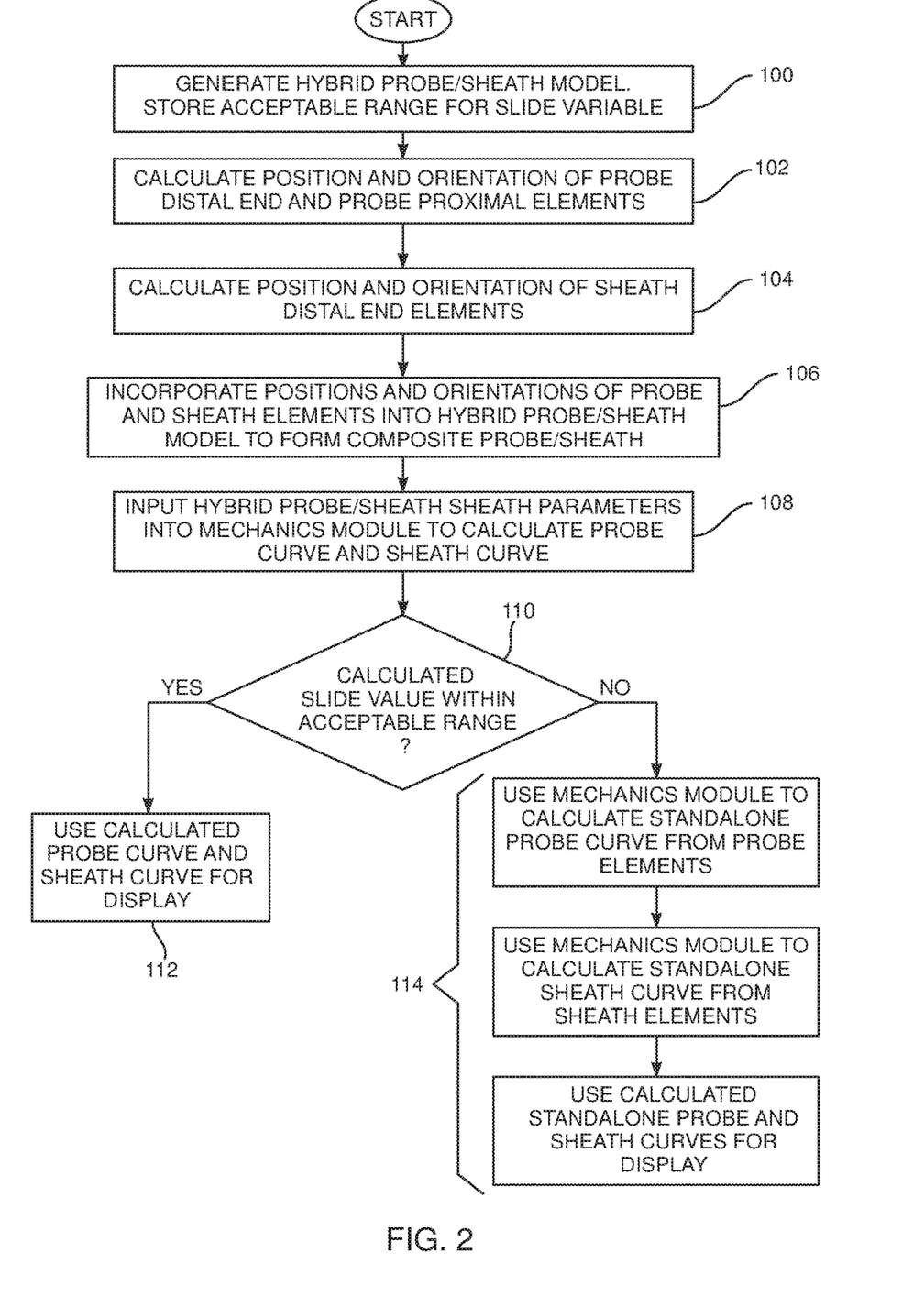
FIG. 2 is a flowchart of steps implemented by a processor in overcoming possibly misaligned sheath and probe images, according to an embodiment of the present invention.
Figure 3:
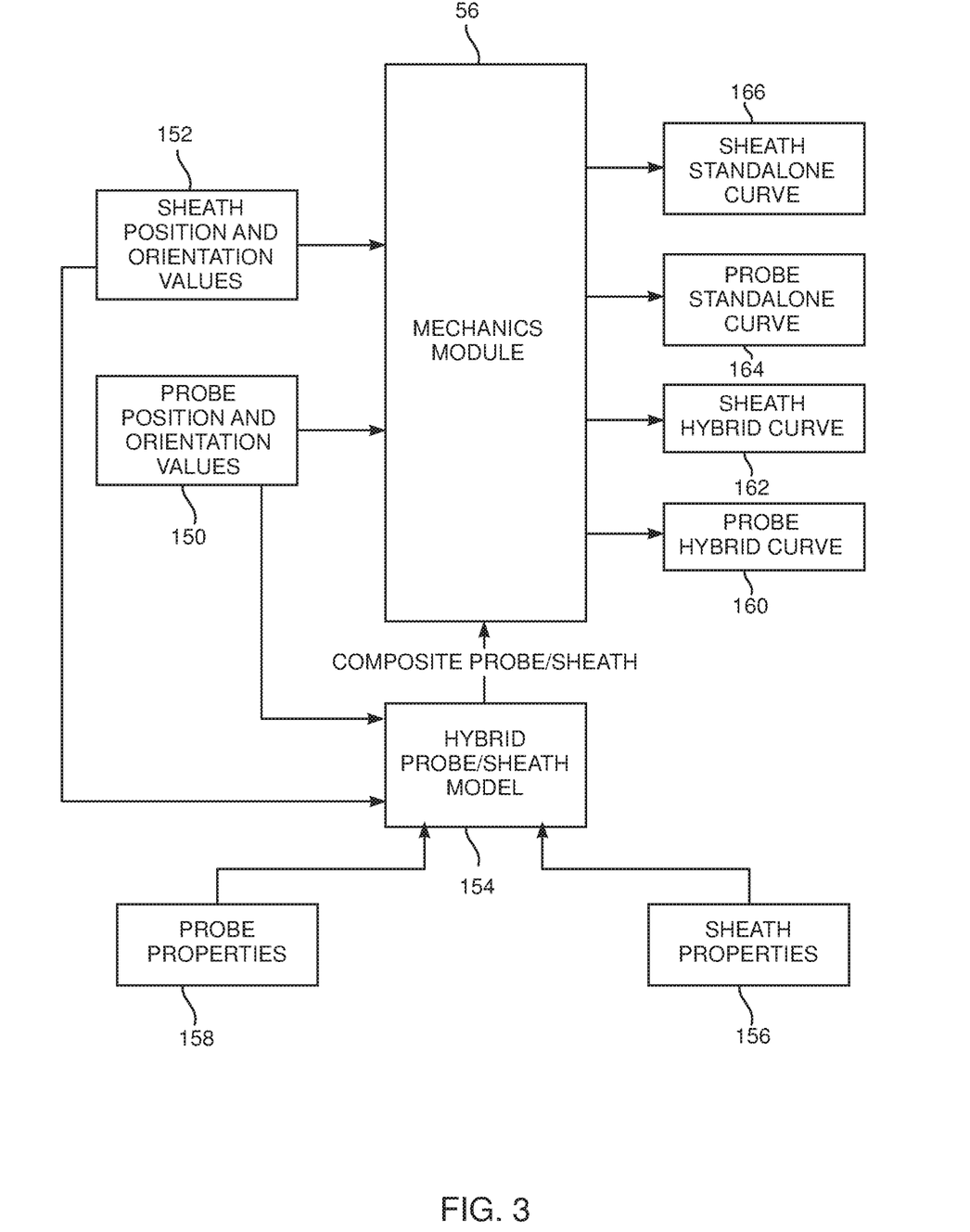
FIG. 3 is a block diagram illustrating some of the steps of the flowchart, according to an embodiment of the present invention.

FIG. 2 is a flowchart of steps implemented by processor 46 in overcoming possibly misaligned sheath and probe images, and FIG. 3 is a block diagram illustrating some of the steps, according to an embodiment of the present invention.

Prior to operating the steps of the flowchart, the two tracking systems of module 52 and 54 are typically registered, for example, as explained in Appendix B.

Prior to operating apparatus 12, in a hybrid model construction step 100, the processor constructs a composite probe/sheath model 154, of a theoretical composite probe/sheath, to be used in mechanics module 56. The model of the composite probe/sheath combines properties 156 of the sheath, i.e., its mechanical properties and the positions of electrodes 28, and properties 158 of the probe, i.e., its mechanical properties and the positions of transducers 24 and 26.

It will be appreciated that since probe 20 slides within sheath 21, the two entities are inherently aligned in practice. It will also be appreciated that since the probe slides within the sheath, the selection of which properties are used in the model depends on the position of the probe distal end with respect to the sheath distal end. For example, if the probe distal end is within the sheath, the mechanical properties of the probe are not used or are given a small weight in comparison to a weight given to the mechanical properties of the sheath.

In all cases, regardless of the position of the probe distal end, the positions of the probe transducers and of the sheath electrodes may be used in the model. Since magnetic sensors give significantly more precise position values compared to electrode position values, in the example considered here the model gives a substantially higher weight to the probe distal positions, derived from magnetic sensor 24, compared to those of the sheath electrode positions. In general, including cases where the sheath has magnetic sensors, the model gives more weight to positions derived from the magnetic sensors compared to positions derived from electrodes.

In step 100 the probe and the sheath are modeled as a single shaft. The probe sensors are fixed on this shaft, but the sheath sensors, electrodes 28 (which are fixed relative to each other), are free to slide on this shaft. The processor operates with mechanics module 56, using the method described in U.S. Pat. No. 8,478,379 and in Appendix A, in this case with an additional optimization parameter—a slide variable s—incorporated into the cost function described therein.

Thus, equation (8) of Appendix A becomes equation (A):

$$\text{Cost}(x_0, r_k, d, s) = \lambda^{int} E^{int} + \lambda^{pos} E^{pos} + \lambda^{or} E^{or} \quad (A)$$

where s is a slide variable and the other variables of equation (A) are as defined for equation (8).

The slide variable s has a value that is related to the distance between the probe and sheath distal ends, as determined from the measurements of sensor 24 and electrodes 28. In step 100 the processor stores an acceptable range of values for the slide variable.

In one embodiment a minimum slide variable value of s corresponds to the distal tip of the probe being inside the sheath, typically in the middle between the proximal and distal electrodes 28 of the sheath. A maximum slide variable value of s corresponds to the probe being out of the sheath such that there is no more than approximately 50 mm (typical value) between the probe's most proximal electrode 26 and the sheath's most distal electrode 28. This ensures that no more than approximately 50 mm of the probe shaft without electrodes will be interpolated.

For example, if the probe's most proximal electrode is at 40 mm from its tip, and the sheath's most distal electrode is at 12 mm from its tip, then the slide variable s maximum value is set to be 78 mm.

In a probe calculation step 102 of the flowchart, the processor uses modules 52 and 54 to calculate position and orientation values 150 for the distal end and proximal sections of probe 20.

In a sheath calculation step 104, the processor uses module 54 to calculate position and orientation values 152 of the distal end of sheath 21. (If the sheath has magnetic sensors, the processor uses module 52 to calculate position and orientation values for these sensors.)

In a model construction step 106, the processor uses the values from steps 102 and 104, and the hybrid model generated in step 100, to formulate a theoretical composite probe/sheath.

In a module input step 108 parameters of the composite probe/sheath are input to mechanics module 56, and the module calculates three-dimensional coordinates for a probe curve and for a sheath curve by minimizing the modified cost function generated in step 100. While minimizing the cost function, an optimal value of the slide variable is also calculated. The calculated slide variable value is used to divide the calculated shaft shape into probe and sheath portions for display.

The values from steps 102 and 104 are also input to the mechanics module.

In a decision step 110, the processor checks if the slide variable is within the range defined in step 100.

If decision step 110 returns positive, then in a first presentation step 112 the processor presents a probe curve 160 and a sheath curve 162, as calculated in step 108, on screen 62.

If the decision step returns negative, i.e., the probe is too far from the sheath or is well inside the sheath, then in second presentation steps 114 the processor generates separate "standalone" probe and sheath curves 164 and 166 (from the separate probe and sheath values input to module 56 in step 108) and presents these curves on screen 62.

Figure 4A:
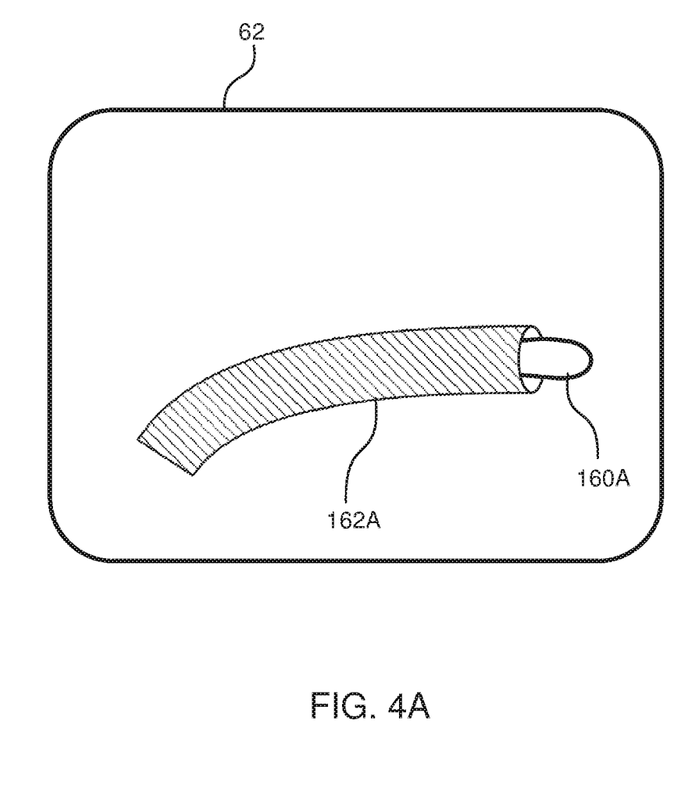
FIGS. 4A and 4B are schematic diagrams illustrating displays on a screen, according to an embodiment of the present invention.
Figure 4B:
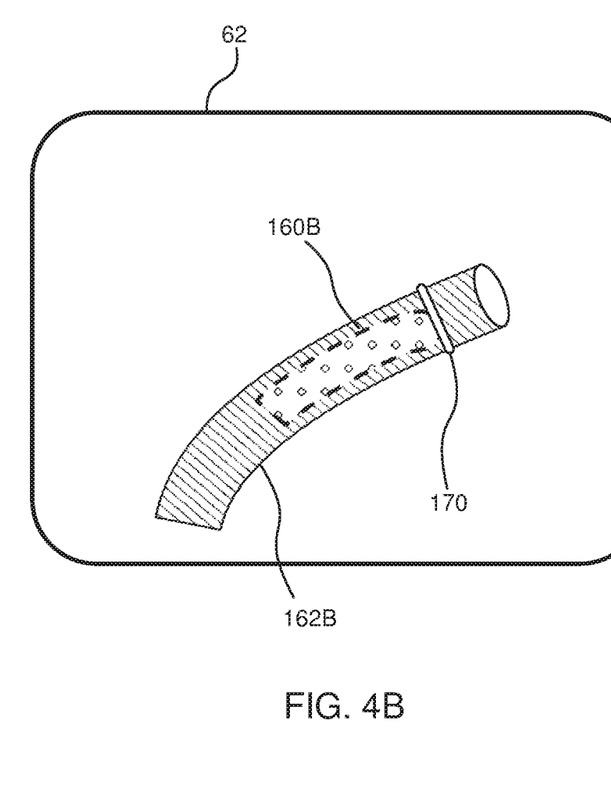

FIGS. 4A and 4B are schematic diagrams illustrating displays on screen 62 when decision step 110 returns positive, according to an embodiment of the present invention. In FIG. 4A, probe distal end 22 has exited sheath distal end 53. In this case a probe curve 160A is shown as exiting from, and aligned with, a sheath curve 162A, In FIG. 4B, probe distal end 22 has not exited sheath distal end 23. In this case a sheath curve 162B may be rendered at least partially transparent, so that the position of a probe curve 160B within the sheath is visible. Alternatively or additionally the processor may overlay a marker 170, indicating the position of the distal end of probe 20, on sheath curve 162B.

APPENDIX A

Figure 5A:
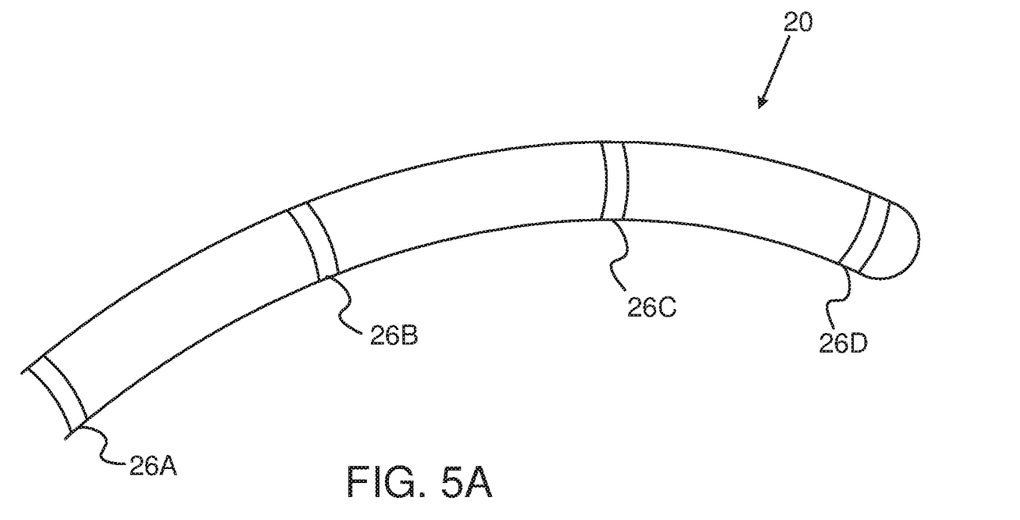
FIGS. 5A and 5B are diagrams that schematically show a probe deviating from its free shape, according to an embodiment of the present invention.
Figure 5B:
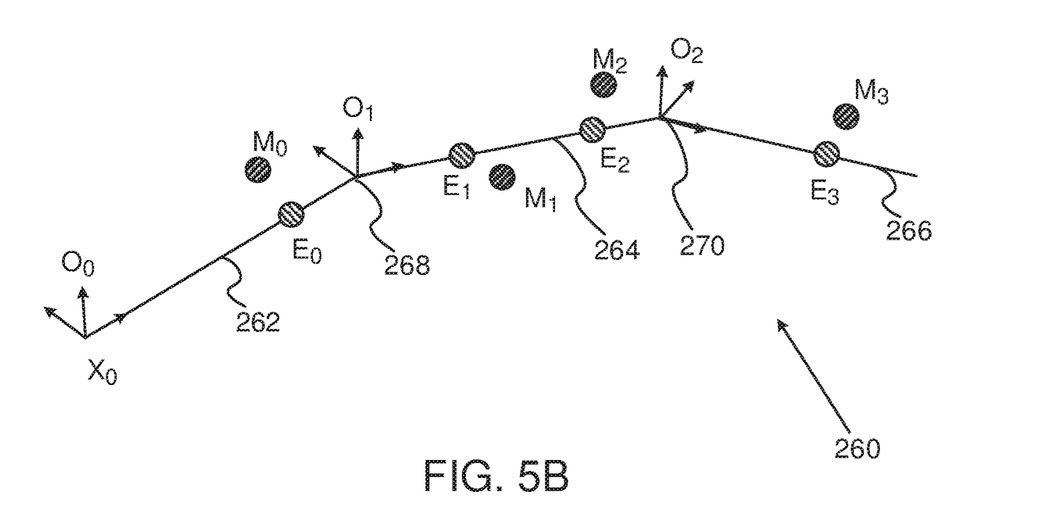

FIGS. 5A and 5B are diagrams that schematically show probe 20 deviating from its free shape, according to an embodiment of the present invention. FIG. 5A shows a representation of the actual curvature of probe 20 in myocardium 16, wherein probe 20 comprises electrodes 26A, 26B, 26C, 26D, which serve as position transducers in this embodiment. FIG. 5B is a diagram of a calculated geometrical model 260 of probe 20. The measured locations of electrodes 26A, 26B, 26C, 26D, based on the signals received by console 48, are respectively represented by points $m_0$, $m_1$, $m_2$ and $m_3$. Alternatively or additionally, in a magnetic position sensing system, the position transducers may comprise single-axis magnetic sensors (SAS), which give position and direction, and/or three-axis magnetic sensors (TAS), which provide position and a complete orientation matrix.

In model 260, points $e_0$, $e_1$, $e_2$ and $e_3$ represent calculated locations of electrodes 26A, 26B, 26C, 26D, based on the measured locations of points $m_0$, $m_1$, $m_2$ and $m_3$. A cost function (described below) in accordance with an embodiment of the present invention is used to find the best match between the point $e_j$ and $m_j$. Model 260 comprises straight rigid sections 262, 264 and 266, connected by joints 268 and 270 that allow rotation (bending and twisting). The position of section 262 is described by position vector $x_0$, and the orientation of section 262 is given by a matrix $o_0$. Orientation matrix $o_0$ is a local reference frame of section 262 with its $\hat{x}$ and $\hat{y}$ axes being perpendicular to section 262, and the $\hat{z}$ axis pointing along section 262. Section 264 starts at the end of section 262 (i.e., via connecting joint 268), and its orientation is given by matrix $o_1$. Section 266 starts at the end of section 264 (i.e., via connecting joint 270), and its orientation is given by matrix $o_2$. Matrices $o_0$, $o_1$ and $o_2$ describe the actual state (i.e., shape) of the probe, wherein external forces cause the probe to deviate from its free state (i.e., in which no external forces are applied to the probe). Although model geometry 260 comprises three sections, alternative model geometries may comprise either fewer than three or more than three sections.

Embodiments of the present invention determine the best match between the points $e_j$ and the measurements $m_j$ within the constraints of a probe model. Note that the calculated locations of points $e_0$, $e_1$, $e_2$ and $e_3$ are constrained by the model to be on the sections 262, 264 and 266, but the actual position transducers (i.e., electrodes 26A, 26B, 26C, 26D) may not be precisely at these points. The physical properties of probe 12 in its free state are defined by the parameters $\{N, L_k, G_k(d), P_k\}$ wherein:

N—Number of sections.

$L_k$—Section lengths (need not be equal), $0 \leq k < N$.

$G_k(d)$—Rotation matrix as a function of the deflection parameters d for deflectable probes (or a constant matrix for pre-shaped probes), $1 \leq k < N$. This matrix represents the relative rotation between section k and section (k−1) when no external forces are applied (i.e., probe free shape).

$P_k$—List of position transducers on section k, where $0 \leq k < N$. Each position transducer is represented by its distance from the section start, its type (for example, electrode or magnetic sensor), and its relative importance (its weight in calculating a cost function, denoted by $w_j^{model}$, discussed infra). The list for each section can contain any number of position transducers, including zero.

The physical properties of probe 20 are described by the parameters $\{A_k, B_k\}$ which represent the resistance of a joint between section k and section (k−1) against bending and twisting, respectively.

Frequently, as shown in FIG. 5B, the actual position of probe 20 (as defined by the locations of electrodes 26A, 26B, 26C, 26D) differs from points $m_0$, $m_1$, $m_2$ and $m_3$. In embodiments of the present invention, a probe model is defined, describing the physical characteristics of probe 20, and processor 46 applies a probe mechanics algorithm to achieve the best match between the probe model and the measurements. The result is a minimal cost state for probe 20, which describes the location and shape (i.e., an actual shape different from the free shape) of probe 20 and its deflection values (for a deflectable probe). A deflection value is a model parameter that describes a family of probe free shapes for a deflectable probe. Typically, a single deflection parameter affects several joints. Any joint rotation that differs from the rotation defined by the deflection parameter increases the cost function.

The probe mechanics algorithm uses a cost function, which is a weighted combination of intrinsic energy, position error and orientation error. Intrinsic energy represents the deviation of probe 20 from its free shape. Position error represents the error in position coordinates between the position transducer locations, given by the probe model and state, and the actual position measurements. Finally, orientation error represents the error in angular orientation coordinates between the position transducer orientations, given by the probe model and state, and the actual orientation measurements.

Figure 6:
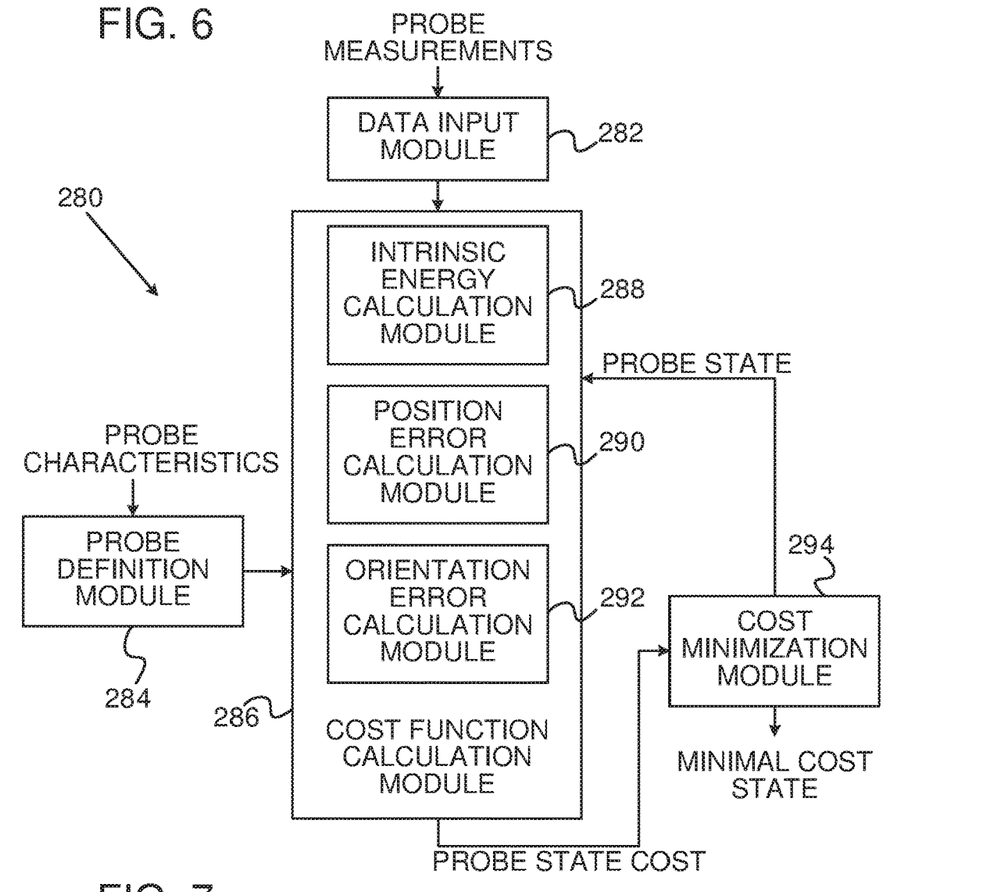
FIG. 6 is a block diagram that schematically illustrates functional components that are used in detection and compensation for artifacts experienced during position sensing of a probe, according to an embodiment of the present invention.

FIG. 6 is a block diagram 280 that schematically illustrates functional components that are used in detection and compensation for artifacts experienced during position sensing of a probe, according to an embodiment of the present invention. Specifically, this figure shows functional elements of software that runs on processor 46 in the course of determining the position of probe 20. These functional elements are described in greater detail with reference to the figures that follow.

Figure 7:
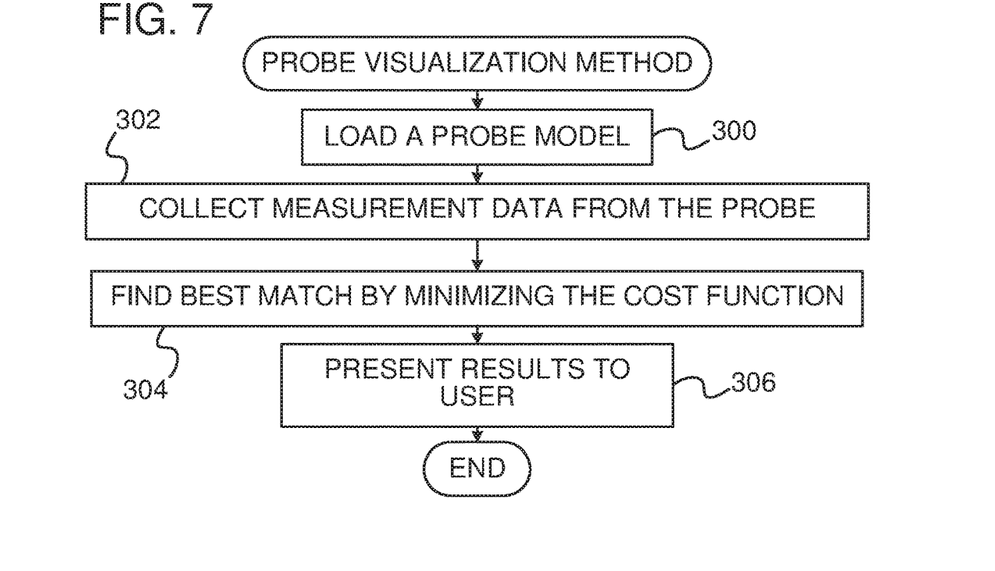
FIG. 7 is a flowchart that schematically illustrates a method for visualizing a probe placed within a patient, according to an embodiment of the present invention.

FIG. 7 is a flowchart that schematically illustrates a method for visualizing probe 20 placed within patient 18, according to an embodiment of the present invention. First, a probe model is pre-loaded into a probe definition module 284 (step 300). As discussed supra, the probe model describes the structure and the physical properties of probe 20 and is typically defined specifically for the type of catheter or other probe that is to be used. Medical professional 14 may select the model, for example, from a pre-defined list of options.

As medical professional 14 moves probe 12 in patient 18, a data input module 282 collects output position signals from electrodes 26A, 26B, 26C, 26D at regular intervals (step 302). For each position transducer 26A, 26B, 26C, 26D defined in the probe model, data input module 282 receives a corresponding position measurement. The measurement can include a position vector (all types of transducers), direction (SAS) and/or full orientation (TAS). In addition, a measurement weight is associated with each measurement, depending on the confidence level of the measurement. The weight has a high value for precise measurements, and a low value for measurements with large expected error. Missing measurements will have weight of zero. The measurement parameters include:

$m_j$—Position measurement $m_j^{or}$—Orientation measurement (may include the full orientation or only direction)

$w_j^{msr}$—Weight of the measurement

After data input module 282 receives the inputs, a cost function calculation module 286 defines a probe state cost by applying a cost function to calculate the quality of the match between the probe model defined in probe definition module 284 and position data received from data input module 282 (step 304). This match defines the shape of the probe with the lowest cost according to the model, which in turn gives corrected coordinates of the points along the length of the probe that correspond to the locations of the position transducers. The probe state describes the location and shape of probe 20 and its deflection values (for a deflectable probe). Processor 46 determines the probe state at step 304. The state is given by the variables $\{x_0, r_k, d\}$:

$x_0$—The position of the first section starting point (i.e., in FIG. 5B.

$r_k$—The orientation of section k relative to section k−1 for 0<k<N section and the global orientation of the first section for k=0:

$$r_k \equiv \begin{cases} o_{k-1}^T \cdot o_k & 0 < k < N \\ o_0 & k = 0 \end{cases}$$

d—The values of the deflection parameters (for deflectable probes). These values do not affect the position and shape of probe 20, but they do affect the calculation of the cost function and thus affect the outcome of the probe mechanics algorithm.

As part of step 304, cost function calculation module 286 feeds the probe state cost to a cost minimization module 294, which applies a minimization algorithm to the cost function in order to find a minimal cost probe state that achieves a minimum value of the cost function (i.e., a best match). Finally, after determining the minimal cost probe state, screen 62 (FIG. 1) presents the position of probe 20 in patient 18 (step 306). Typically, the probe position is shown in the form of an icon on the display, having a location, orientation and shape corresponding to model 260.

Figure 8:
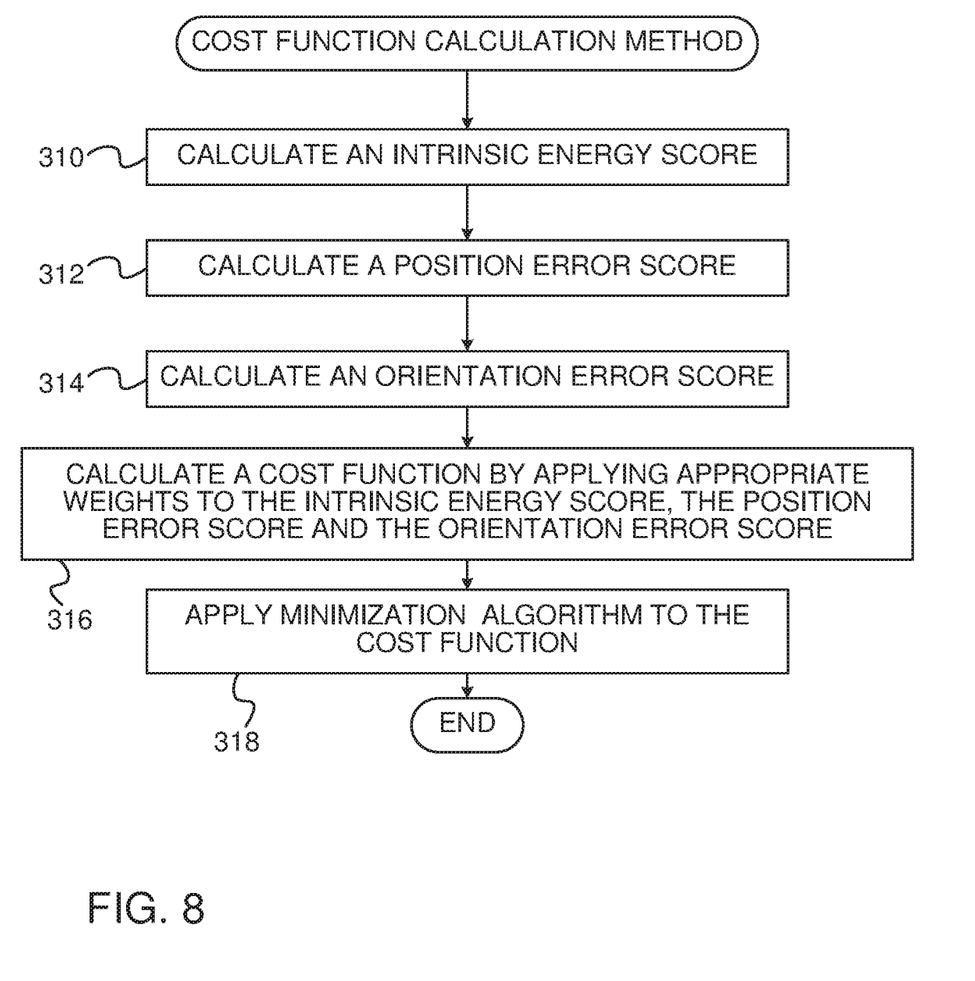
FIG. 8 is a flowchart that schematically illustrates a method by which a cost function calculation module applies a cost function to probe measurements received by a data input module, according to an embodiment of the present invention.

FIG. 8 is a flowchart that schematically illustrates a method by which cost function calculation module 286 applies a cost function to probe measurements received by data input module 282, according to an embodiment of the present invention. The cost function depends on the probe model, the position measurements and the probe state. Minimizing the cost function with respect to the probe state $\{x_0, r_k, d\}$ achieves the best match between the probe model and the measurements. The calculation of the cost function also depends on a set of adaptive weights that are assigned to the measurements. The adaptive weights may dynamically change during the course of the cost function minimization and allow the algorithm to ignore measurements that totally disagree with the probe model (described hereinbelow). The adaptive weights are denoted by $w_j^{adaptive}$.

The cost function has three parts: intrinsic energy, position error and orientation error. First, an intrinsic energy calculation module 288 calculates an intrinsic energy score (step 310), which represents the deviation of probe 20 from its free shape (or a family of free shapes parameterized by deflection variables—for deflectable probes). For joints 268 and 270, the orientation difference between the actual relative orientation and the current deflection is calculated as:

$$dr_k = r_k^T \cdot G_k(d) \quad (1)$$

Intrinsic energy calculation module 88 converts this orientation difference to the bend and twist angles:

$$\{\alpha_k, \beta_k\} = \text{Angles}(dr_k) \quad (2)$$

The following is a definition of the function Angles(r) wherein r is a unitary 3×3 matrix that represents rotation:

$$\{\alpha, \beta\} \equiv \text{Angles}\left( \begin{bmatrix} r_{11} & r_{12} & r_{13} \\ r_{21} & r_{22} & r_{23} \\ r_{31} & r_{32} & r_{33} \end{bmatrix} \right)$$

$$\alpha = \arccos(r_{33})$$

$$\beta = \arctan(r_{11}(1+r_{33}) - r_{31}r_{13}, r_{12}(1+r_{33}) - r_{32}r_{13})$$

where:

arctan(x,y) is the angle between the vector(x,y) and the x axis. (3)

Returning to the cost function, intrinsic energy calculation module 288 calculates the intrinsic energy score using the probe model parameters $\{A_k, B_k\}$.

$$E^{int} = \sum_{k=1}^{N-1} A_k \alpha_k^2 + B_k \beta_k^2 \quad (4)$$

A position error calculation module 290 then calculates a position error score (step 312), which represents the position error between the locations of the position transducers given by the probe model and state, and the actual measurements. Position error calculation module 290 denotes the position of electrodes 26A, 26B, 26C, 26D according to the probe model and state as $e_j$ and the corresponding measurements as $m_j$. Position error calculation module 290 calculates the weighted position error as follows:

$$E^{pos} = \sum_{j=0}^{M-1} w_j^{model} w_j^{msr} w_j^{adaptive} (e_j - m_j)^2 \quad (5)$$

where M is the number of position transducers.

An orientation error calculation module 292 then calculates an orientation error score (step 314), which represents the orientation error between the position of electrodes 26A, 26B, 26C, 26D, given by the probe model and state, and the actual measurements $m_j$ received by data input module 282. The orientation of the various points along probe 20, represented by the probe model, is a discontinuous function, which has abrupt changes at model joints (unlike the position). After calculating the orientations of all the relevant position transducers $e_j^{or}$ according to the model, orientation error calculation module 292 calculates the angular difference with respect to the measured orientation $m_j^{or}$:

$$\{a_j, b_j\} = \text{Angles}((e_j^{or})^T \cdot m_j^{or}) \quad (6)$$

and the total orientation error:

$$E^{or} = \sum_{j=0}^{M-1} w_j^{model} w_j^{msr} w_j^{adaptive} (a_j^2 + b_j^2) \quad (7)$$

Cost function calculation module 286 then calculates a cost function as a weighted combination of the three parts (i.e., intrinsic energy, position error and orientation error) (step 316):

$$\text{Cost}(x_0, r_k, d) = \lambda^{int} E^{int} + \lambda^{pos} E^{pos} + \lambda^{or} E^{or} \quad (8)$$

The values $\{\lambda^{int}, \lambda^{pos}, \lambda^{or}\}$ describe the relative importance of deviation of probe 20 from its free shape vs. the position and orientation errors.

As discussed supra, cost function calculation module 286 feeds the calculated cost function (i.e., the probe state cost) to minimization module 294, which minimizes the function Cost($x_0, r_k, d$) with respect to the probe state variables in order to achieve the best match between the probe model and the actual measurements received by data input module 282 (step 318). The minimization can be done by any suitable numerical method. In one embodiment of the present invention, for example, cost function calculation module 286 uses the Broyden-Fletcher-Goldfarb-Shanno (BFGS) minimization algorithm.

Since minimizing the cost function in step 318 employs an iterative algorithm (i.e., each iteration of the algorithm improves the estimate of the solution), and the position and shape of probe 20 change slowly between measurements, the inventors have found that it is usually sufficient to apply only one iteration of the cost function minimization algorithm for each successive measurement. After each minimization iteration, cost minimization module 294 feeds a probe state to cost function calculation module 286, which may change the adaptive weights of the measurements according to the individual transducer position errors. Typically, the weights corresponding to impedance-sensing electrodes are adapted, while more accurate sensors, such as magnetic position sensors, retain a weight of 1.

Cost function calculation module 286 performs the weight adaptation procedure as follows:
1. Compute Initial New Weights $$w_j^{new} = \max\left(\exp\left(\frac{(e_j - m_j)^2}{2\sigma_j^2}\right), 0.0001\right) \quad (9)$$

wherein the value $\sigma$ is larger for sensors with a large expected error, thereby allowing a greater error prior to a decrease in a corresponding adaptive weight.

2. Normalize the Initial Weights $$w_j^{new} \leftarrow \frac{w_j^{new}}{\text{mean}(w_j^{new})} \quad (10)$$

3. Limit Each Weight from Above by 1

$$w_j^{new} \leftarrow \min(w_j^{new}, 1) \quad (11)$$

4. Update the Adaptive Weights $$w_j^{adaptive} \leftarrow 0.9 w_j^{adaptive} + 0.1 w_j^{new} \quad (12)$$

This adaptation procedure allows the minimization process to ignore position transducers that consistently give large errors, yet does not allow it to ignore too many position transducers.

APPENDIX B

Figure 9:
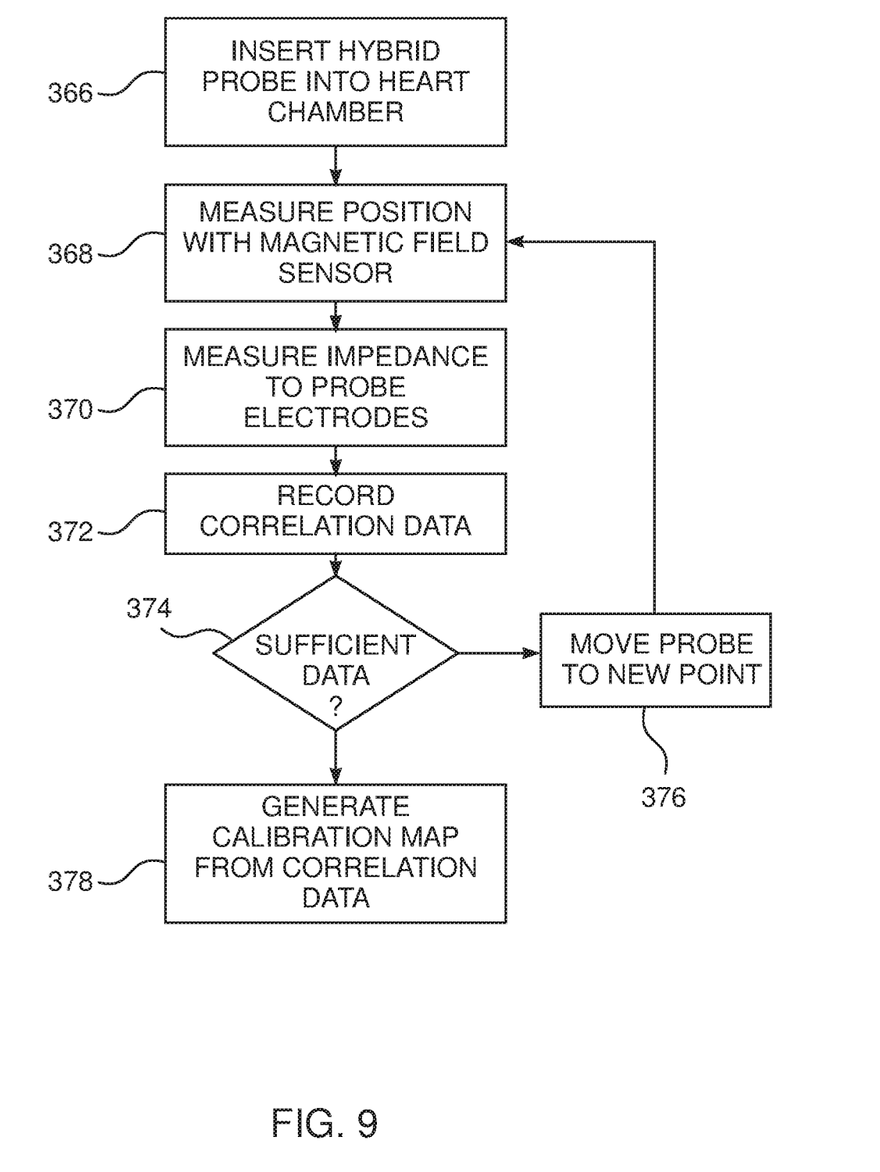
FIG. 9 is a flowchart showing a method for generating a calibration map, according to an embodiment of the present invention.

FIG. 9 is a flowchart showing a method for generating a calibration map, according to an embodiment of the present invention. In an initial step 366, a hybrid probe, herein assumed to be probe 20 (FIGS. 1A, 1B), is inserted into a chamber of myocardium 16 (or into another body cavity, as appropriate) prior to performance of a procedure on the chamber. In a magnetic measurement step 368, magnetic field sensor 24 is used to determine the position coordinates of the probe, and thus find the specific locations of probe electrodes 26. Impedance measurements at these electrodes are then taken in an impedance measurement step 370, by measuring currents from the electrodes to a set of body-surface electrodes. Next, in a correlation step 372, the impedance measurements are correlated with the electrode positions determined in step 368. The correlations register the magnetic measurement system with the impedance measurement system.

In a decision step 374, a determination is made as to whether sufficient data for a calibration map has been collected, based on the needs of the procedure. If more data is required, the hybrid probe is moved to a new position in the heart chamber, at a positioning step 376, and steps 368 through 374 are repeated. In practice, steps 368 and 370 are performed continuously, so that steps 366 through 376 may be carried out in a continuous process, as well, while moving the probe gradually through different parts of the cavity that is to be mapped.

Once sufficient data has been collected, a calibration map is generated in a mapping step 378. Typically, the calibration map comprises a grid of coordinates, determined by magnetic sensing, that are registered with a set of impedance measurements (relative to the body-surface electrodes) recorded at each point in the grid. Alternatively, the grid may be inverted, so that the map indicates the actual, calibrated position coordinates for each set of impedance measurements.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for correcting image misalignment between a sheath and probe inserted into a body, comprising:
   calculating locations of first sensors attached to a probe that has been inserted into a human patient;
   calculating positions of second sensors attached to a sheath via which the probe is inserted;
   calculating respective shapes of the probe and the sheath, to achieve a best fit to the calculated probe sensor locations and sheath sensor positions, while restricting the probe to pass through the sheath, wherein calculating the respective shapes of the probe and the sheath comprises minimizing a cost function to determine a best match between a calculated location and a measured location, the cost function is a weighted combination of intrinsic energy, position error and orientation error and incorporating a slide variable having a value related to a distance between distal ends of the probe and sheath into the cost function;
   correcting image misalignment between the sheath and the probe using the calculated respective shapes of the probe and the sheath; and
   presenting a corrected image of the sheath accurately aligned with the probe and having no discrepancies in the image of the probe relative to the sheath.

2. The method according to claim 1, wherein calculating the locations of the first sensors attached to the probe comprises positioning at least one magnetic sensor on the probe, and calculating the locations using a magnetic tracking system.

3. The method according to claim 1, wherein calculating the positions of the second sensors comprises positioning at least one electrode on the sheath, generating a plurality of currents from the at least one electrode, and calculating the positions in response to the plurality of currents in a current tracking system.

4. The method according to claim 1, wherein calculating the respective shapes of the probe and the sheath comprises modeling the probe and the sheath as a single shaft.

5. The method according to claim 4, wherein the first sensors are fixed on the shaft.

6. The method according to claim 4, wherein the second sensors are free to slide on the shaft.

7. The method according to claim 1, wherein a minimum value of the slide variable corresponds to a distal tip of the probe being inside the sheath.

8. The method according to claim 1, wherein a maximum value of the slide variable corresponds to the first sensors and the second sensors being separated by no more than a preset distance.

9. An apparatus for correcting image misalignment between a sheath and probe inserted into a body, comprising:
   a probe configured to be inserted into a human patient;
   first sensors attached to the probe;
   a sheath via which the probe is inserted;
   second sensors attached to the sheath; and
   a processor, configured to:
      calculate locations of the first sensors attached to the probe,
      calculate positions of the second sensors attached to the sheath,
      calculate respective shapes of the probe and the sheath, to achieve a best fit to the calculated probe sensor locations and sheath sensor positions, while restricting the probe to pass through the sheath, wherein calculating the respective shapes of the probe and the sheath comprises minimizing a cost function to determine a best match between a calculated location and a measured location, the cost function is a weighted combination of intrinsic energy, position error and orientation error and incorporating a slide variable having a value related to a distance between distal ends of the probe and sheath into the cost function, and
      correct image misalignment using the calculated respective shapes of the probe and the sheath to present an image of the sheath accurately aligned with the probe and having no discrepancies in the image of a probe relative to a sheath.

10. The apparatus according to claim 9, wherein calculating the locations of the first sensors attached to the probe comprises positioning at least one magnetic sensor on the probe, and calculating the locations using a magnetic tracking system.

11. The apparatus according to claim 9, wherein calculating the positions of the second sensors comprises positioning at least one electrode on the sheath, generating a plurality of currents from the at least one electrode, and calculating the positions in response to the plurality of currents in a current tracking system.

12. The apparatus according to claim 9, wherein calculating the respective shapes of the probe and the sheath comprises modeling the probe and the sheath as a single shaft.

13. The apparatus according to claim 12, wherein the first sensors are fixed on the shaft.

14. The apparatus according to claim 12, wherein the second sensors are free to slide on the shaft.

15. The apparatus according to claim 9, wherein a minimum value of the slide variable corresponds to a distal tip of the probe being inside the sheath.

16. The apparatus according to claim 9, wherein a maximum value of the slide variable corresponds to the first sensors and the second sensors being separated by no more than a preset distance.

* * * * *